United States Patent [19]

Magistro

[11] 4,158,645

[45] Jun. 19, 1979

[54] CATALYST FOR THE PREPARATION OF ETHYLENE AND VINYL CHLORIDE FROM ETHANE

[75] Inventor: Angelo J. Magistro, Brecksville, Ohio

[73] Assignee: The B. F. Goodrich Company, Akron, Ohio

[21] Appl. No.: 887,166

[22] Filed: Mar. 16, 1978

Related U.S. Application Data

[62] Division of Ser. No. 669,895, Mar. 24, 1976, Pat. No. 4,102,936.

[51] Int. Cl.$^2$ .................... B01J 21/04; B01J 23/10; B01J 23/74; B01J 23/84
[52] U.S. Cl. .................................................. 252/462
[58] Field of Search ........................................ 252/462

[56] References Cited

U.S. PATENT DOCUMENTS

| | | | |
|---|---|---|---|
| 3,207,811 | 9/1965 | Bajars | 260/683.3 X |
| 3,420,901 | 1/1969 | Schulz | 260/656 R |
| 3,904,553 | 9/1975 | Campbell et al. | 252/468 X |
| 4,119,570 | 10/1978 | Kroenke et al. | 252/462 X |

Primary Examiner—W. J. Shine
Attorney, Agent, or Firm—Alan A. Csontos

[57] ABSTRACT

Ethane is reacted with oxygen and a chlorine source in the presence of a solid solution catalyst containing iron cations which is stabilized with lanthanum and/or lanthanides and modified with selected metal cations, to yield ethylene, vinyl chloride, and other valuable by-products. Conversion of ethane to products approaches 100 percent, ethylene is prepared in up to 90 mole percent yield, and the combined yield of ethylene, vinyl chloride and ethyl chloride is over 90 mole percent.

10 Claims, No Drawings

CATALYST FOR THE PREPARATION OF ETHYLENE AND VINYL CHLORIDE FROM ETHANE

This is a division, of application Ser. No. 669,895, filed Mar. 24, 1976, now U.S. Pat. No. 4,102,936.

BACKGROUND OF THE INVENTION

Vinyl chloride ($CH_2=CHCl$) is prepared using a number of well known processes. Two familiar processes are (1) the hydrochlorination of acetylene and (2) the oxychlorination of ethylene to form dichloroethane which in turn is dehydrohalogenated to form vinyl chloride (see C. A. Schildknecht, *Vinyl and Related Polymers*, John Wiley and Sons, Inc. N.Y., N.Y. (1952), pages 388-390 and U.S. Pat. No. 2,847,483). As acetylene is more expensive than ethylene, the latter process is economically favored, and much activity is noted in this art area (see U.S. Pat. Nos. 3,634,330; 3,454,663; 3,448,057; and 3,624,170). Ethylene, in turn, can be prepared by the oxydehydrogenation of ethane (see U.S. Pat. No. 3,769,362). Although high yields of ethylene are particularly desired, processes which use ethane as a feed stock can produce not only ethylene, but also can directly produce vinyl chloride and other valuable products such as ethylene dichloride, ethyl chloride, and the like. The ethylene, ethylene dichloride, and ethyl chloride can be readily reacted to form more vinyl chloride.

The present invention is directed to an improved process for the preparation of ethylene and vinyl chloride from ethane which process employs a solid solution catalyst containing iron stabilized with lanthanum and/or lanthanides and modified with select metal cations. The catalysts exhibit improved activity and/or long lifetime. Catalysts containing iron or lanthanum are known to the art; see U.S. Pat. Nos. 3,907,713; 3,849,339; 3,769,362; 3,703,593; 3,658,934; 3,658,933; 3,207,809; 2,847,483; and 2,674,633; and British Pat. No. 1,039,369. However, none of these patents disclose a solid solution catalyst. An article in the Journal of The American Ceramic Society, Vol. 43, No. 7 (1960), page 367, discloses compounds of lanthanum and iron. A recently issued patent, U.S. Pat. No. 3,904,553, discloses certain specific solid solutions as catalysts.

SUMMARY OF THE INVENTION

The invention comprises an improved catalyst and process for the preparation of ethylene and vinyl chloride from ethane. The catalyst is a solid solution catalyst containing iron cations substituted for cations of the host lattice which catalyst is stabilized with lanthanum and/or lanthanides and modified with one or more metal cations selected from the group consisting of lithium, magnesium, chromium, manganese, cobalt, and copper. Use of these catalysts in the process of the invention produces yields of over 85 mole percent of ethylene and over 90 combined mole percent of ethylene and vinyl chloride. The catalysts can remain active for up to 300 hours or more without substantial loss of iron.

DETAILED DESCRIPTION OF THE INVENTION

Ethane is reacted with oxygen and a chlorine source and in the presence of a solid solution catalyst containing iron which is stabilized with lanthanum and/or lanthanides and modified with selected metal cations to prepare ethylene, vinyl chloride, and other valuable by-products. Depending upon feed and reactor conditions, about 30 to about 85 mole percent yield of ethylene and over a 90 mole percent total yield of ethylene and vinyl chloride can be obtained. Conversion of ethane to products can approach 100 mole percent.

In the process, ethane, oxygen and a chlorine source are placed into a reactor vessel containing a solid solution catalyst of the invention. The process contemplates the use of standard techniques concerning the type of operation, reactor size and design, and the like. The process can be operated as a batch process, but is preferably conducted as a continuous process wherein reactants and products are continuously added and withdrawn. The solid solution catalyst can be fixed in a bed, it can be supported, or it can be present as particles that can readily fluidize during operation. A preferred embodiment of the process is to employ the solid solution catalyst in particulate form that will fluidize in the process thereby establishing maximum contact with the reactants. Such processes are known as fluid bed processes, and the reactors designed for such are known as fluid bed reactors. A typical reactor is designed such that one or more gaseous reactants is introduced in the reactor below the catalyst bed, and the gas pressurized through the bed lifting and suspending the catalyst in the reactor volume. Other reactants can be added at appropriate levels above, below, or any point in the fluid catalyst bed. Normally, products are withdrawn from the top portion of the reactor and collected or further treated as desired.

Although the process contemplates the use of known operating techniques and reaction conditions, certain conditions are herein stated as useful and practical. The reactants comprise ethane, oxygen (usually used in the form of air), and a chlorine source. The chlorine source is preferably hydrogen chloride gas. Using one mole of ethane as a basis, the hydrogen chloride is used at from about 0.1 mole to about 10 moles or more. More preferably, the hydrogen chloride is used at a level of from about 0.5 mole to 5 moles per mole of ethane. In general, as a higher ratio of hydrogen chloride to ethane is used, the yield of vinyl chloride and other chlorinated products increases and the yield of ethylene decreases. However, levels of use of hydrogen chloride above 5 moles per mole of ethane also increase the amount of hydrogen chloride to recycle. Excellent results have been obtained using about 1 to about 4 moles of hydrogen chloride per mole of ethane. As both ethylene and vinyl chloride can be prepared in significant amounts using the catalysts and as the yield of ethylene to vinyl chloride is highly dependent upon the hydrogen chloride to ethane ratio in the reactant feed, the process can be termed either an oxydehydrochlorination process to prepare ethylene or an oxychlorination process to prepare vinyl chloride.

Oxygen, preferably in the form of dry air, is used at from about 0.1 mole to about 1.5 moles of oxygen to one mole of ethane. A more preferred level is from about 0.5 mole to about 1 mole. The use of levels of oxygen of about 1 mole per mole of ethane is preferred in an oxychlorination process. In an oxydehydrochlorination process excellent results have been obtained using a level of oxygen of about 0.5 to 0.6 mole per mole of ethane.

Ethane, oxygen, and hydrogen chloride are put into the reactor as reactants. Temperature of the reaction ranges from about 400° C. to about 650° C., and more preferably from about 475° C. to about 600° C. Materials withdrawn from the reactor in the product stream comprise ethylene, vinyl chloride, chlorinated products such as ethylene dichloride and ethyl chloride, carbon oxides (CO and $CO_2$), water, and unreacted ethane and hydrogen chloride.

The improved feature of the process of the invention is the use as a catalyst of a solid solution catalyst containing iron cations substituted for cations in the host lattice which catalyst is stabilized with lanthanum and/or lanthanides and modified with selected metal cations. The catalyst is basically a solid solution of iron cations in a host lattice. This is in contrast to catalysts wherein an active ingredient such as cupric chloride or iron oxide is merely absorbed onto the surface of a support structure or material. The difference is crucial and can be distinguished both in the physical state of the catalyst and in the activity of the catalyst.

The solid solution catalyst is a true solution wherein iron cations are substituted for host lattice ions in the catalyst structure. An X-ray diffraction pattern of a solid solution catalyst is characterisitic of the diffraction pattern of the host lattice. For example, a solid solution catalyst of $Fe_2O_3$ in $\alpha$-$Al_2O_3$ will exhibit an X-ray diffraction pattern characteristic of $\alpha$-$Al_2O_3$. In contrast, if $Fe_2O_3$ is merely absorbed onto $\alpha$-$Al_2O_3$, the X-ray diffraction pattern will show the presence of both $Fe_2O_3$ and $\alpha$-$Al_2O_3$.

A distinguishing feature of the solid solution catalysts of the invention, i.e., solid solution catalysts containing iron and stabilized with lanthanum and/or lanthanides and modified with select metal cations, is in the increased selectivity and/or retention of iron by the catalyst upon use. For example, an $\alpha$-$Al_2O_3$ solid solution catalyst containing iron cations which is stabilized with lanthanum cations and modified with cobalt, used at reaction conditions of 1 mole ethane/0.6 mole oxygen/1.5 mole hydrogen chloride, lost about 0.2% by weight of its original iron content after over 100 hours of use. In contrast, a catalyst which is a solid solution of iron in $\alpha$-$Al_2O_3$ stabilized with lanthanum but not modified lost about 3% of its original iron content after about 100 hours of use at the same set of conditions. In further contrast, a catalyst consisting of a simple solid solution of iron in $\alpha$-$Al_2O_3$ lost about 4% by weight of its iron content under the same conditions. In yet further contrast, a catalyst comprised of ferric oxide merely absorbed onto $Al_2O_3$, operating under the same set of conditions, lost over 8% by weight of its original iron content after about 100 hours of use.

Solid solution catalysts containing iron cations can be of different types. The iron exists as ferric ($Fe^{+3}$) and/or ferrous ($Fe^{+2}$) ions. The ferric ion is the active ion in the catalyst. However, as the ferrous ion can oxidize to a ferric ion in the process, the use of solid solution catalysts containing ferrous ions is within the scope of the invention.

In the solid solution catalyst containing iron cations there is direct substitution of iron ions for host lattice ions. An example of this catalyst is $(Fe_x{}^{+3}M_{2-x}{}^{+3})O_3$ wherein x is greater than 0 and less than 2 and M is a metal such as Al or Cr. An example of this is a solid solution catalyst of ferric oxide ($Fe_2O_3$ in aluminum oxide ($Al_2O_3$). As the ferric ion is much greater in size than an aluminum $^{+3}$ ion, the solubility of the ferric ion in aluminum oxide is limited. Hence, the solid solution catalysts of the example wherein M is aluminum encompass materials of the formula wherein x has an upper limit of about 0.15.

The solid solution catalyst containing iron is stabilized with lanthanum and/or a lanthanide. Although the lanthanum or lanthanide is an integral part of the catalyst, it is believed that the lanthanum or lanthanide does not enter into solid solution with the host lattice as does the iron. Characterization of the catalysts of this invention will be discussed further in a subsequent section of the application.

The lanthanum and lanthanides can be employed in the solid solution catalysts singly or as mixtures of the metals. The lanthanides are elements 58 to 71 of the Periodic Table. More preferably, the lanthanides used are cerium, praeseodymium, neodymium, and erbium. Excellent results have been obtained using a catalyst of $Fe_2O_3$ in $\alpha$-$Al_2O_3$ stabilized with lanthanum.

The solid solution catalyst containing iron and stabilized with lanthanum or a lanthanide is further modified with select metal cations. The use of these cations results in a catalyst having improved selectivity for the formation of vinyl chloride and/or increased catalyst lifetime. The metal cations employed are selected from the group consisting of lithium, magnesium, chromium, manganese, cobalt, and copper. Excellent results have been obtained using cobalt to modify the catalyst to achieve significant increases in catalyst lifetime, and manganese to modify the catalyst to achieve more selectivity for vinyl chloride.

Although the selected metal cation is an integral part of the catalyst, it is believed that the selected metal does not enter into solid solution with the host lattice as does the iron.

Solid Solution Catalyst Identification and Characterization

The solid solution catalysts of the invention contain iron and have X-ray diffraction patterns characteristic of the host lattice material. Solid solutions are known to exist (see C. S. Barrett, *Structure of Metals, Crystallographic Methods, Principles, and Data*, 2nd Ed., McGraw-Hill Book Co., Inc., N.Y., N.Y. (1952) at pages 220 et seq. and U.S. Pat. No. 3,904,553).

The catalyst is first identified and characterized by analyzing it to determine what elements it contains. This can be done using well known techniques such as chemical analysis, atomic absorption spectroscope, X-ray fluorescence spectroscopy, and optical microscopy. For example, the solid solution catalyst of iron oxide in aluminum oxide, stabilized with lanthanum and modified with cobalt, would show iron, lanthanum, aluminum, cobalt, and oxygen to be present in the catalyst. The presence and quantity of iron in the catalyst can be readily determined using a standard method of chemical analysis such as the dichromate method for the determination of iron. The amount of iron in the solid solution catalysts is limited by the solubility of the ions in the host lattice. The solid solution catalysts of the invention can contain from about 0.1 percent to 20 percent by weight and more preferably from about 0.5 percent to about 10 percent by weight of iron in the catalyst expressed as iron oxide. The catalyst can contain similar levels of lanthanum and/or lanthanide expressed as the oxide. The selected metal cation is present in a range of from about 0.05 percent to about 3 percent by weight and more preferably in from about 0.1 percent to about 0.5 percent by weight of the catalyst expressed as the oxide of the selected metal.

The second step of identification and characterization involves running an X-ray diffraction scan on the catalyst. The X-ray diffraction scan will show a pattern of peaks, which peaks have positions and intensities distinctive of the crystalline phases which are present. The X-ray diffraction peak positions and intensities of the catalyst can be compared to peak positions and intensities of known crystalline phases that are published (in the ASTM Powder Diffraction File, for example), or that are experimentally obtained. For example, a catalyst comprised of iron oxide merely impregnated on aluminum oxide will have an X-ray diffraction pattern of peak positions showing the distinct peak positions and intensities of iron oxide and aluminum oxide crystalline phases.

In contrast, the X-ray diffraction pattern of a solid solution catalyst containing iron shows the positions of the X-ray diffraction peaks in the solid solution catalyst to be shifted from the peak positions in the X-ray diffraction pattern of the host lattice. The shift in peak positions may be accompanied by changes in the relative intensities of the peaks, but the intensity changes are generally small.

The shift in X-ray diffraction peak positions when solid solutions are formed results from the expansion (or contraction) of the dimensions of the unit cell of the crystalline phase of the host lattice. The dimensions of the unit cell of the host lattice are changed due to the substitution of iron cations for cations of the host lattice. If the cation is larger than the cation it displaces, the unit cell dimensions will increase in size to accommodate the larger cation. The amount of expansion (or contraction if the iron cation is smaller than the host lattice cation it displaces) of the unit cell dimensions can be determined by calculating the lattice parameters of the unit cell of the solid solution phase and comparing these lattice parameters to the lattice parameters of the unit cell of the host. A change in lattice parameters due to iron substitution in a crystalline host lattice is frequently in accordance with Vegard's law (see page 221 of the above-cited reference). Since a change in the lattice parameters causes a change in the X-ray diffraction peak positions, a quick comparison of the X-ray diffraction pattern of the catalyst and the pattern of the host lattice will show whether a solid solution catalyst has been prepared.

Alternately, a more accurate method of confirming the preparation of a solid solution catalyst is to experimentally run X-ray diffraction scans of the prepared catalyst and of the host lattice and then calculate the lattice parameters of each. If the values obtained for the lattice parameters of the catalyst and host lattice are different, a solid solution catalyst has been prepared. If the geometry and dimensions (lattice parameters) of the unit cell of the host lattice is not known, it can be determined using established methods for indexing and interpreting X-ray diffraction patterns (see L. V. Azaroff and M. J. Buerger, *The Powder Method in X-Ray Crystallography* McGraw-Hill Book Co., Inc. N.Y., N.Y. (1958), chapters 6 to 13). The high $2\theta$ values (where $\theta$ is the Bragg angle) are normally used to calculate the lattice parameters.

In the case of a solid solution catalyst stabilized with lanthanum and/or a lanthanide and modified with a selected metal, the X-ray diffraction pattern will clearly show the presence of the solid solution, which is the primary crystalline phase, and will additionally show the presence of crystalline lanthanum and/or lanthanide and selected metal compounds which are present in detectable amounts. For example, in the case of a solid solution catalyst of $Fe_2O_3$ in $\alpha$-$Al_2O_3$ stabilized with lanthanum and modified with cobalt, the X-ray diffraction pattern will show the presence of the $Fe_2O_3$ in $\alpha$-$Al_2O_3$ solid solution crystalline phase, the crystalline compounds of lanthanum such as $La_2O_3$ and $LaAlO_3$, and crystalline cobalt oxide.

In summary, the solid solution catalysts of the invention can be identified and characterized by (1) the presence of iron, lanthanum and/or lanthanides, and the selected metal in the catalyst and (2) the X-ray diffraction pattern of the catalyst. The iron is present as cations substituted in the host lattice for cations of the host lattice. The iron content can be measured using standard analysis techniques. The X-ray diffraction pattern of the solid solution catalyst will exhibit peak positions characteristic of the host lattice but shifted due to the presence of the iron cations in the host lattice. Lattice parameters calculated for the host lattice and the solid solution catalyst will differ. The X-ray diffraction pattern of the solid solution catalysts of the invention will exhibit extraneous peaks in the pattern due to formation of crystalline compounds other than the solid solution catalyst itself, such as lanthanum oxide or lanthanide oxides, and selected metal oxides.

Preparation of Solid Solution Catalysts of the Examples

The solid solution catalysts used in the Examples were prepared by first impregnating a host lattice precursor with an iron salt, a lanthanum salt and a selected metal salt or precursor that yields the oxides upon heating, then heating the impregnated host lattice precursor to about 550° C. followed by heating to 1200° C. or more. The first heat treatment converts the salts to oxides, and initiates conversion of the host lattice precursor to the host lattice. The second heat treatment completes the formation of the host lattice and produces a rearrangement of the metal atoms between the metal ions in the host lattice and the iron ions. The catalyst prepared is a solid solution catalyst containing iron, stabilized with lanthanum and/or lanthanides and modified with the selected metal. The catalyst has a distinctive X-ray diffraction pattern.

The solid solution catalyst can be prepared in other different ways. Another method is to physically admix iron oxide, lanthanum or a lanthanide oxide, the selected metal oxide, and the host lattice material and heat the mix to allow dissolution and substitution of the iron ions for those of the host lattice, and formation of the stabilized and modified catalyst. Heating conditions vary for the nature of the host lattice employed, but typically are above about 1100° C.

A third method of preparation is to use the so-called sol-gel process wherein an iron salt, lanthanum and/or lanthanide salt, selected metal salt, and a salt precursor of the host lattice are mixed together as solutions and a base is added to co-precipitate out a mixture of the corresponding hydrated oxides. For example, ferric nitrate, lanthanum nitrate, cobalt nitrate, and aluminum nitrate can be dissolved in water and ammonium hydroxide added to the solution to co-precipitate a mixture of hydrated iron, lanthanum, cobalt, and aluminum oxides. The mix is then heated to above about 1100° C. to perfect dissolution and substitution of the iron ions for aluminum ions.

A fourth method is to dissolve a selected metal salt in a solvent such as water or ethanol and use the solution to impregnate a preformed solid solution catalyst already stabilized with lanthanum and/or lanthanides then dry and heat the mix to cause the metal salt to decompose upon heating to yield the oxide.

In all of these methods a metal oxide precursor can be used in place of the metal oxide per se. The precursor, which is typically a salt of the metal, decomposes on heating to yield the oxide form of the metal. Examples of iron oxide precursors are iron chloride, iron sulfate, iron formate, iron oxalate, iron citrate, iron nitrate, and the like. Precursors of the oxides of lanthanum or lanthanides and of the selected metals can also be employed. Examples of lanthanum oxide precursors are lanthanum nitrate, lanthanum chloride, lanthanum sulfate, lanthanum oxalate, and the like. Examples of selected metal oxide precursors are lithium nitrate, lithium oxalate, magnesium nitrate, magnesium chloride, chromium acetylacetonate, chromium dichloride, manganese chloride, manganese oxalate, manganese nitrate, cobalt chloride, cobalt nitrate, and cobalt oxalate.

The solid solution catalysts of the invention can be used in the process in the form of a fixed bed, a fluidized bed, on a fixed support, on a fluidized support, or in a number of ways well known to the art. Although in the examples the process used is a fluidized bed process, it is understood that other well known techniques can be employed. The following Examples are given to further illustrate the invention.

EXAMPLES

Solid solution catalysts were used in an oxydehydrochlorination process to react ethane to ethylene, and in an oxychlorination process to react ethane to vinyl chloride. The reactions were conducted in a fluid bed reactor wherein the ethane, oxygen used in the form of air, and anhydrous HCl were premixed at a set molar ratio of reactants and the mixture fed into a heated reactor near the bottom. The catalyst used was in the form of particles of a size passing between 80 mesh and 325 mesh screens. Contact times in the reaction were from about 4 seconds to about 10 seconds. Products were withdrawn from the top of the reactor as gases, scrubbed with water and analyzed using a gas chromatograph. The process was run as a continuous process for times of 1 hour up to 300 hours or more per run.

The following examples detail experiments conducted using various mole ratios of reactants, various temperatures and times of reaction, and different solid solution catalysts.

EXAMPLE I

Experiments were conducted to compare ethane conversion, yield of ethylene and vinyl chloride obtained, and retention of iron on use among (a) a catalyst of this invention, (b) an unmodified but lanthanum stabilized solid solution catalyst, and (c) an impregnated catalyst. All catalysts contained about 2% by weight of $Fe_2O_3$ in $Al_2O_3$.

The catalyst of the invention was prepared by the following procedure. A solution of 16.0 grams of $La(NO_3)_3$—$6H_2O$, 0.75 grams of $Co(NO_3)_2$—$6H_2O$, and 14.9 grams of $Fe(NO_3)_3$—$9H_2O$ dissolved in about 125 milliliters of ethanol was added to 141.1 grams of $Al_2O_3$—$3H_2O$ (sold by Alcoa Co. as C-31) and the ethanol evaporated off. The mixture was then heated at 560° C. for 16 hours to dehydrate the alumina trihydrate and to decompose the ferric nitrate, cobalt nitrate, and lanthanum nitrate to ferric oxide, cobalt oxide, and lanthanum oxide. The catalyst was then further heated at 1200° C. for 16 hours to cause formation of the solid solution catalyst.

The unmodified but lanthanum stabilized solid solution catalyst of iron oxide in α-aluminum oxide was prepared in the same manner as recited above but without any cobalt oxide precursor present. Hence, the catalyst is not modified with cobalt as is the catalyst of the present invention.

The impregnated catalyst employed in the example was prepared by impregnating aluminum oxide with a solution of ferric nitrate, drying the mix, and then heating the mix for 16 hours at 550° C. The preparation is similar to the preparation of the solid solution catalysts except that no heat treatment at 1200° C. was done. X-ray diffraction analysis of the impregnated catalyst showed two distinct phases, i.e., the impregnated catalyst was a mixture of $Fe_2O_3$ and $Al_2O_3$.

The catalysts were individually placed into a reactor and the reactants fed into the reactor at a mix of 1 mole ethane/0.6 mole of oxygen (as air)/1.5 moles of anhydrous hydrogen chloride. The reaction was run as an oxydehydrochlorination reaction process to obtain high yields of ethylene. Contact time throughout the runs was about 5 seconds. Temperature of reaction was about 550° C. Results are given in the following tables.

| | Modified and Stabilized Solid Solution Catalyst | | |
|---|---|---|---|
| | Mole % | % Yield of | |
| Time (Hrs.) | Conversion of Ethane | Ethylene | Vinyl Chloride |
| 2 | 82.0 | 81.6 | 6.9 |
| 20 | 83.2 | 80.9 | 6.2 |
| 44.5 | 84.6 | 80.5 | 6.2 |
| 72 | 80.2 | 80.6 | 5.9 |
| 96 | 86.1 | 79.0 | 6.6 |
| 119 | 77.3 | 79.5 | 6.3 |
| 148 | 82.3 | 79.7 | 6.1 |

| | Unmodified But Stabilized Solid Solution Catalyst | | |
|---|---|---|---|
| | Mole % | % Yield of | |
| Time (Hrs.) | Conversion of Ethane | Ethylene | Vinyl Chloride |
| 1.5 | 89.7 | 75.4 | 14.7 |
| 5 | 86.9 | 78.8 | 12.7 |
| 27 | 88.6 | 80.9 | 9.7 |
| 48 | 86.8 | 81.4 | 9.3 |
| 71 | 86.0 | 81.0 | 7.6 |
| 96.5 | 82.3 | 81.9 | 6.0 |
| 105 | 86.5 | 82.4 | 7.5 |
| 125 | 85.2 | 80.6 | 6.6 |

| | Impregnated Catalyst | | |
|---|---|---|---|
| | Mole % | % Yield of | |
| Time (Hrs.) | Conversion of Ethane | Ethylene | Vinyl Chloride |
| 18.5 | 53.9 | 72.3 | 2.1 |
| 42 | 57.4 | 71.8 | 2.3 |
| 66.5 | 51.9 | 73.6 | 2.4 |
| 90.5 | 53.6 | 73.6 | 2.5 |

The data shows that the use of the solid solution catalysts results in significantly higher mole percent conversion of ethane to products and higher yield of ethylene and vinyl chloride than the use of the impregnated catalyst. Although the stabilized solid solution catalysts exhibit comparable results in conversion and yield data, the modified solid solution catalysts of the invention have much improved retention of iron on use and show activity for longer periods of time when in use. The catalyst of the invention lost only 0.2% of its original iron content after 165 hours of use. The stabilized but unmodified catalyst used above lost 3.1% of its original iron content after 97 hours and 4.7% of its original iron content after 203 hours of use (a solid solution catalyst containing iron but no lanthanum or selected metal lost over 3.6% of its iron content in about 100 hours of use under similar conditions). The simple catalyst of iron oxide impregnated on aluminum oxide lost 8.4% of its original iron content after 90 hours of use.

EXAMPLE II

The reactant feed ratio used in the conversion process can vary considerably. The main effects of varying this ratio are to change the mole percent conversion of ethane, the comparative yields of ethylene and vinyl chloride obtained, and to change the rate of iron loss. A series of experiments were conducted using stabilized and modified solid solution catalysts of the invention in a fluidized bed process with a contact time of about 4 seconds and at a temperature of 550° C. The reactant feed ratio varied as 1 ethane/0.5 to 0.9 oxygen/1.5 to 3 hydrogen chloride.

As the amount of HCl is increased in a series, conversion of ethane generally increases, the yield of ethylene decreases, and the rate of iron loss increases. As the amount of $O_2$ is increased, conversion of ethane generally increases while the yield of ethylene increases and the yield of vinyl chloride decreases.

EXAMPLE III

As mentioned in the above examples, as the molar ratio of HCl to ethane increases the comparative yields of ethylene and vinyl chloride change. In Example I, the molar ratio of HCl to ethane was 1.5 to 1 and the process was termed an oxydehydrochlorination reaction in which a high yield of ethylene was promoted. In this example the molar ratio of HCl to ethane is set at 4 to 1 and the process can be termed an oxychlorination reaction in which a high yield of vinyl chloride is promoted.

Comparative results were obtained between the stabilized and modified catalyst of the invention and a stabilized but unmodified solid solution catalyst. The catalysts employed were similar to the respective catalysts used in Example I. The catalysts were individually placed into a reactor and the reactants fed into the reactor at a mix of 1 mole ethane/1 mole oxygen (as air)/4 moles anhydrous hydrogen chloride. Contact time in the runs was about 5 seconds, and reaction temperature was about 550° C. Results are given in the following tables.

| Reactant Feed Ratio Ethane/Oxygen/Hydrogen Chloride | Mole % Conversion of Ethane | % Yield Of Ethylene | % Yield Of Vinyl Chloride | Combined Yield Of Ethylene and Vinyl Chloride |
|---|---|---|---|---|
| 2% $Fe_2O_3$ in α-$Al_2O_3$ Stabilized with 4% $La_2O_3$ and Modified with 0.5% CoO | | | | |
| 1/0.5/1.5 | 70.1 | 73.3 | 7.2 | 80.5 |
| 1/0.6/1.5 | 74.7 | 81.5 | 5.9 | 87.4 |
| 1/0.6/2.5 | 82.2 | 84.2 | 5.4 | 89.6 |
| 1/0.7/3 | 87.5 | 80.7 | 5.0 | 85.7 |
| 2% $Fe_2O_3$ in α-$Al_2O_3$ Stabilized with 4% $La_2O_3$ and Modified with 0.5% $Cr_2O_3$ | | | | |
| 1/0.5/1.5 | 63.9 | 80.2 | 4.0 | 84.2 |
| 1/0.6/1.5 | 78.0 | 80.6 | 4.7 | 85.3 |
| 1/0.6/2.5 | 74.9 | 77.4 | 2.4 | 79.8 |
| 1/0.5/3 | 46.0 | 73.7 | 2.2 | 75.9 |
| 1/0.9/3 | 96.7 | 70.5 | 8.4 | 78.9 |
| 2% $Fe_2O_3$ in α-$Al_2O_3$ Stabilized with 4% $La_2O_3$ and Modified with 0.5% MnO | | | | |
| 1/0.6/1.5 | 92.2 | 82.8 | 10.6 | 93.4 |
| 2% $Fe_2O_3$ in α-$Al_2O_3$ Stabilized with 4% $La_2O_3$ and Modified with 0.5% CuO | | | | |
| 1/0.5/1.5 | 60.8 | 79.6 | 5.9 | 85.5 |
| 1/0.6/1.5 | 67.9 | 77.4 | 5.7 | 83.1 |

| | | Modified and Stabilized Solid Solution Catalyst | | |
|---|---|---|---|---|
| Time (Hrs.) | Mole % Conversion of Ethane | % Yield of Ethylene | % Yield of Vinyl Chloride | Combined Yield of Ethylene and Vinyl Chloride |
| 20 | 98.4 | 53.0 | 26.2 | 79.2 |
| 46 | 97.4 | 55.5 | 21.9 | 77.4 |
| 71.5 | 95.0 | 62.7 | 17.1 | 79.8 |
| 94.5 | 93.1 | 63.4 | 12.7 | 76.1 |

| | | Unmodified but Stabilized Solid Solution Catalyst | | |
|---|---|---|---|---|
| Time (Hrs.) | Mole % Conversion of Ethane | Ethylene | Vinyl Chloride | Combined Yield of Ethylene and Vinyl Chloride |
| 4.5 | 99.9 | 43.6 | 30.3 | 73.9 |
| 27.5 | 99.9 | 48.2 | 28.8 | 77.0 |
| 51 | 99.5 | 55.9 | 21.5 | 77.4 |
| 75 | 98.8 | 61.2 | 17.8 | 79.0 |
| 97 | 98.1 | 61.8 | 13.1 | 74.9 |

The data shows that the use of both catalysts give good yields of ethylene and vinyl chloride. However, the modified catalyst of the invention lost only 9.4% of its original iron content after 94 hours of use while the unmodified catalyst lost 12.5% of its original iron content after 97 hours of use.

EXAMPLE IV

Manganese is one of the more preferred selected metals to be used to modify the catalysts of the invention. The use of manganese to modify stabilized solid solution catalysts yields a catalyst having long life (excellent retention of iron on use), good activity, and improved selectivity for vinyl chloride production. A catalyst prepared as in Example I, comprised of 2% $Fe_2O_3$ in $\alpha$-$Al_2O_3$ stabilized with 4% $La_2O_3$ and modified with 0.5% MnO, was employed in a fluid bed reactor process for preparing ethylene from ethane. The temperature of reaction was about 550° C., and contact time was about 5 seconds. The following results were obtained.

| Time (Hrs.) | Mole % Conversion of Ethane | % Yield of Ethylene | % Yield of Vinyl Chloride |
|---|---|---|---|
| 2 | 87.6 | 79.7 | 10.7 |
| 20.5 | 88.9 | 81.9 | 10.7 |
| 53.5 | 87.7 | 82.7 | 9.8 |
| 76 | 84.0 | 82.8 | 7.9 |
| 97.5 | 85.8 | 85.9 | 7.1 |
| 126 | 90.9 | 82.6 | 9.9 |
| 150 | 92.3 | 82.3 | 10.4 |
| 179 | 90.4 | 82.9 | 9.5 |

EXAMPLE V

The level of use of the selected metal as a modifier for the catalyst can have an effect on the performance of the catalyst. Although the selected metal cation can be present in the catalyst in from about 0.05% to about 3 percent by weight of the catalyst (weight percent expressed as the oxide of the selected metal), the metal is more preferably employed in the lower end of the range. Excellent results are obtained when the selected metal is present at from about 0.1% to about 0.5% by weight. The following runs employ catalysts of 2% by weight of $Fe_2O_3$ in $\alpha$-$Al_2O_3$ stabilized with 4% by weight of $La_2O_3$ and modified by either 0.2% by weight or 0.5% by weight of $Cr_2O_3$. Reaction temperature is 550° C. and contact times are about 5 seconds.

EXAMPLE VI

The temperature of the ethane to ethylene conversion reaction has an effect on conversion and yields obtained in the process. Generally, temperatures between 500° C. and 600° C. are preferred, and a reaction temperature of about 550° C. offers a good balance of mole % conversion of ethane and high ethylene yield and combined yield of ethylene and vinyl chloride. The following results were obtained using 2% $Fe_2O_3$ in $\alpha$-$Al_2O_3$ catalyst stabilized with 4% $La_2O_3$ and modified with 0.2% $Li_2O$.

| Reactant Feed Ratio | Temperature (°C.) | Mole % Conversion Of Ethane | % Yield of Ethylene | % Yield of Vinyl Chloride | Combined Yield Of Ethylene and Vinyl Chloride |
|---|---|---|---|---|---|
| (ethane/ $O_2$/HCl) | | | | | |
| 1/0.6/1.5 | 525 | 89.4 | 77.2 | 14.6 | 91.8 |
| 1/0.7/4 | 550 | 85.6 | 80.7 | 12.3 | 93.0 |
| | 500 | 94.7 | 72.8 | 17.3 | 90.1 |
| | 525 | 96.6 | 71.8 | 20.4 | 92.2 |
| | 550 | 99.1 | 67.6 | 25.8 | 93.4 |

I claim:

1. A solid solution catalyst consisting essentially of iron cations substituted for aluminum cations in a host lattice of $\alpha$-$Al_2O_3$ and having an iron content of from about 0.1 percent to 20 percent by weight expressed as the oxide; stabilized with a total lanthanide content of from about 0.1 percent to 20 percent by weight expressed as the oxide; and modified with a total content of one or more metal cations selected from the group consisting of lithium, cobalt, copper, magnesium, chromium, and manganese of from about 0.05 percent to about 3 percent by weight expressed as the oxide; and having an X-ray diffraction pattern having peak positions different than that of the host lattice, all weight percents based upon the weight of the catalyst.

2. A solid solution catalyst of claim 1 wherein the iron content of the catalyst is from about 0.5 percent to about 10 percent by weight of the catalyst, expressed as the oxide.

3. A solid solution catalyst of claim 2 having iron cations substituted for aluminum cations in $\alpha$-$Al_2O_3$ and stabilized with from about 0.5 percent to about 10 percent by weight expressed as the oxide of lanthanum, cerium, praeseodymium, neodymium, erbium, or mixtures thereof.

4. A solid solution catalyst of claim 3 modified with from about 0.1 percent to about 0.5 percent by weight of cobalt oxide or manganese oxide.

5. The solid solution catalyst of claim 4 consisting essentially of iron cations in an $\alpha$-$Al_2O_3$ host lattice stabilized with lanthanum oxide and modified with cobalt oxide.

6. The solid solution catalyst of claim 4 consisting essentially of iron cations in an $\alpha$-$Al_2O_3$ host lattice

| Ethane/Oxygen/HCl Feed Ratio | Mole % Conversion of Ethane | % Yield of Ethylene | % Yield of Vinyl Chloride |
|---|---|---|---|
| 0.2% by weight Modified Catalyst | | | |
| 1/0.5/1.5 | 80.4 | 85.8 | 8.1 |
| 1/0.6/1.5 | 90.4 | 81.9 | 10.7 |
| 0.5% by weight Modified Catalyst | | | |
| 1/0.5/1.5 | 63.9 | 80.2 | 4.0 |
| 1/0.6/1.5 | 75.7 | 78.7 | 4.8 | stabilized with lanthanum oxide and modified with manganese oxide.

7. A solid solution catalyst of claim 3 stabilized with lanthanum oxide.

8. A solid solution catalyst of claim 7 modified with chromium oxide.

9. A solid solution catalyst of claim 7 modified with copper oxide.

10. A solid solution catalyst of claim 7 modified with lithium oxide.

* * * * *